United States Patent
Oonuma (10) Patent No.: US 7,968,051 B2
(45) Date of Patent: Jun. 28, 2011

(54) CLINICAL LABORATORY APPARATUS

(75) Inventor: Takehiko Oonuma, Ujiie-machi (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1461 days.

(21) Appl. No.: 10/998,565

(22) Filed: Nov. 30, 2004

(65) Prior Publication Data

US 2005/0129576 A1 Jun. 16, 2005

(30) Foreign Application Priority Data

Dec. 2, 2003 (JP) .................................. 2003-402805

(51) Int. Cl.
*G01N 35/02* (2006.01)
*G01N 35/08* (2006.01)

(52) U.S. Cl. ................ 422/67; 422/63; 422/64; 436/45; 436/47; 436/49; 436/50; 436/55; 700/266; 702/22

(58) Field of Classification Search .................. None
See application file for complete search history.

(56) References Cited

U.S. PATENT DOCUMENTS

| | | | | |
|---|---|---|---|---|
| 4,908,320 A | * | 3/1990 | Zakowski et al. | 436/45 |
| 5,320,966 A | * | 6/1994 | Mitsumaki et al. | 436/47 |
| 2004/0115095 A1 | * | 6/2004 | Devlin et al. | 422/63 |

FOREIGN PATENT DOCUMENTS

| | | | | |
|---|---|---|---|---|
| JP | 63163147 A | * | 7/1988 | |
| JP | 02087069 A | * | 3/1990 | |
| JP | 7-159416 | | 6/1995 | |

* cited by examiner

*Primary Examiner* — P. Kathryn Wright
(74) *Attorney, Agent, or Firm* — Oblon, Spivak, McClelland, Maier & Neustadt, L.L.P.

(57) ABSTRACT

A clinical laboratory apparatus includes a plurality of reaction cuvettes, a first dispenser, a second dispenser, a controller, and an analyzer. A subject sample and a reagent are mixed in each of the plurality of reaction cuvettes. The first dispenser is configured to dispense the subject sample into each of the plurality of reaction cuvettes. The second dispenser is configured to dispense the reagent into each of the plurality of reaction cuvettes so that the subject sample and the reagent are mixed. The controller is configured to categorize the plurality of reaction cuvettes into at least first and second groups, to designate at least first and second analysis items among two or more analysis items with respect to the subject sample, to control the second dispenser to avoid dispensing the reagent relevant to the first analysis item into the second group of the reaction cuvettes. The analyzer is configured to analyze a mixed result.

9 Claims, 8 Drawing Sheets

| | ANALYSIS ITEMS TO BE MEASURED | | | | | | | | | |
|---|---|---|---|---|---|---|---|---|---|---|
| | ITEM1 | ITEM2 | ITEM3 | ITEM4 | ITEM5 | ITEM6 | ITEM7 | ITEM8 | ... | ITEM49 | ITEM50 |
| SUBJECT SAMPLE 1 | | O | | O | O | | | | | | |
| SUBJECT SAMPLE 2 | | O | O | O | | O | | | | O | |
| SUBJECT SAMPLE 3 | | O | | O | | | O | O | | | |

| | | ITEM1 | ITEM2 | ITEM3 | ITEM4 | ITEM5 | ITEM6 | ITEM7 | ITEM8 | ... | ITEM49 | ITEM50 |
|---|---|---|---|---|---|---|---|---|---|---|---|---|
| SUBJECT SAMPLE 1 | | ANALYSIS ITEMS TO BE MEASURED | | | | | | | | | | |
| ANALYSIS ITEM | REACTION CUVETTE ID NO. | | ○ | ○ | ○ | ○ | | | | | | |
| | | | 1 | | 2 | 3 | | | | | | |
| LINE INFORMATION | | | A | | B | A | | | | | | |
| SUBJECT SAMPLE 2 | | ANALYSIS ITEMS TO BE MEASURED | | | | | | | | | | |
| ANALYSIS ITEM | REACTION CUVETTE ID NO. | | ○ | ○ | | | ○ | | | | ○ | |
| | | | 4 | 5 | | | 6 | | | | 7 | |
| LINE INFORMATION | | | B | A | | | B | | | | A | |
| SUBJECT SAMPLE 3 | | ANALYSIS ITEMS TO BE MEASURED | | | | | | | | | | |
| ANALYSIS ITEM | REACTION CUVETTE ID NO. | | ○ | | ○ | | | ○ | ○ | | | |
| | | | 8 | | 9 | | | 10 | 11 | | | |
| LINE INFORMATION | | | B | | A | | | B | A | | | |

26

| SUBJECT SAMPLE 1 | | ANALYSIS ITEMS TO BE MEASURED | | | | | | | | | |
|---|---|---|---|---|---|---|---|---|---|---|---|
| | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | | ○ | ○ | | | | | | |
| LINE INFORMATION | | | 1 | | 2 | 3 | | | | | | |
| | | | A | | B | A | | | | | | |

| SUBJECT SAMPLE 2 | | ANALYSIS ITEMS TO BE MEASURED | | | | | | | | | |
|---|---|---|---|---|---|---|---|---|---|---|---|
| | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | ○ | | | ○ | | | | ○ | |
| LINE INFORMATION | | | 5 | 4 | | | 6 | | | | 7 | |
| | | | A | B | | | B | | | | A | |

| SUBJECT SAMPLE 3 | | ANALYSIS ITEMS TO BE MEASURED | | | | | | | | | |
|---|---|---|---|---|---|---|---|---|---|---|---|
| | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | | ○ | | | ○ | ○ | | | |
| LINE INFORMATION | | | 9 | | 8 | | | 10 | 11 | | | |
| | | | A | | B | | | B | A | | | |

FIG. 7

| 28 | | ANALYSIS ITEMS TO BE MEASURED | | | | | | | | | |
|---|---|---|---|---|---|---|---|---|---|---|---|
| SUBJECT SAMPLE 1 | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | | ○ | ○ | | | | | | |
| LINE INFORMATION | | | 1 | | 2 | 3 | | | | | | |
| | | | A | | B | A | | | | | | |

| | | ANALYSIS ITEMS TO BE MEASURED | | | | | | | | | |
|---|---|---|---|---|---|---|---|---|---|---|---|
| SUBJECT SAMPLE 2 | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | ○ | | | ○ | | | | ○ | |
| LINE INFORMATION | | | 5 | 6 | | | 7 | | | | 8 | |
| | | | A | B | | | A | | | | B | |

| | | ANALYSIS ITEMS TO BE MEASURED | | | | | | | | | |
|---|---|---|---|---|---|---|---|---|---|---|---|
| SUBJECT SAMPLE 3 | | ITEM1 | ITEM2 | ITEM3 | ITEM4 | ITEM5 | ITEM6 | ITEM7 | ITEM8 | ... | ITEM49 | ITEM50 |
| ANALYSIS ITEM | REACTION CUVETTE ID NO. | | ○ | | ○ | | | ○ | ○ | | | |
| LINE INFORMATION | | | 9 | | 10 | | | 11 | 12 | | | |
| | | | A | | B | | | A | B | | | |

SUBJECT SAMPLE 1

| | ANALYSIS ITEMS TO BE MEASURED | | | | | | | | | | |
|---|---|---|---|---|---|---|---|---|---|---|---|
| | ITEM1 | ITEM2 | ITEM3 | ITEM4 | ITEM5 | ITEM6 | ITEM7 | ITEM8 | ... | ITEM49 | ITEM50 |
| ANALYSIS ITEM REACTION CUVETTE ID NO. | | ○ | | ○ | ○ | | | | | | |
| | | 73 | | 74 | 75 | | | | | | |
| LINE INFORMATION LINE | | A | | B | A | | | | | | |

SUBJECT SAMPLE 2

| | ANALYSIS ITEMS TO BE MEASURED | | | | | | | | | | |
|---|---|---|---|---|---|---|---|---|---|---|---|
| | ITEM1 | ITEM2 | ITEM3 | ITEM4 | ITEM5 | ITEM6 | ITEM7 | ITEM8 | ... | ITEM49 | ITEM50 |
| ANALYSIS ITEM REACTION CUVETTE ID NO. | | ○ | ○ | | | ○ | | | | ○ | |
| | | 77 | 78 | | | 79 | | | | 80 | |
| LINE INFORMATION LINE | | A | B | | | A | | | | B | |

SUBJECT SAMPLE 3

| | ANALYSIS ITEMS TO BE MEASURED | | | | | | | | | | |
|---|---|---|---|---|---|---|---|---|---|---|---|
| | ITEM1 | ITEM2 | ITEM3 | ITEM4 | ITEM5 | ITEM6 | ITEM7 | ITEM8 | ... | ITEM49 | ITEM50 |
| ANALYSIS ITEM REACTION CUVETTE ID NO. | | ○ | | ○ | | | ○ | ○ | | | |
| | | 81 | | 82 | | | 83 | 84 | | | |
| LINE INFORMATION LINE | | A | | B | | | A | B | | | |

CLINICAL LABORATORY APPARATUS

CROSS-REFERENCE TO RELATED APPLICATION

This application is based upon and claims the benefit of priority from prior Japanese Patent Application No. P2003-402805, filed on Dec. 2, 2003, the entire contents of which are incorporated herein by reference.

BACKGROUND OF THE INVENTION

1. Field of the Invention

The present invention relates to a clinical laboratory apparatus and a method of controlling a reagent dispensation regarding two or more analysis items.

2. Discussion of the Background

A clinical laboratory apparatus is typically used to measure concentration or activity of enzyme or agent to be measured included in a subject sample. This measurement is usually achieved by determining, based on measuring light transmission quantity, color tone variation caused by reaction between the subject sample dispensed in a reaction cuvette and reagent relevant to an analysis item.

When various analysis items are measured, using a plurality of reaction cuvettes, one reaction cuvette is assigned to each analysis item at random. Reagent relevant to the analysis item and the subject sample are dispensed for the measurement. After the measurement, the used reaction cuvette is usually cleaned and dried for another measurement. One or more components included in some types of reagent, however, cannot be removed from the reaction cuvette in the ordinary cleaning and dry operation. Such remaining components may react to one or more components included in reagent for another analysis item if the same reaction cuvette is used. In this case, an analysis result of such another analysis item may be affected by the reaction between the remaining component(s) in the reaction cuvette and the one or more components included in the reagent for another analysis item.

For example, as described in Japanese Patent Application Publication No. 2000-287700, when the neutral fat is measured, reagent for analyzing the neutral fat is used in a reaction cuvette. The lipoprotein lipase included in the reagent may be remained or adsorbed in the reaction cuvette without being removed by the ordinary cleaning and dry operation. Accordingly, the adsorbed lipoprotein lipase may affect the measurement of the lipase if the lipase is measured with the reaction cuvette used for the measurement of the neutral fat. This may occur even when the reaction cuvette was used, before the measurement of the lipase, for a measurement of the third analysis item which is not affected by the lipoprotein lipase and is not affectable to the measurement of the lipase.

In order to avoid the above problem, information of a set of one affecting analysis item and one analysis item to be affected is input to and stored in the clinical laboratory apparatus. When a reaction cuvette used for the affecting analysis item comes for a measurement of the analysis item to be affected, the reaction cuvette is skipped so that another reaction cuvette which is not used for the affecting analysis item can be used for the analysis item to be affected. This technique is described, for example, in Japanese Patent No. 2509591.

One or more components remaining on an internal surface of the skipped reaction cuvette may not be removed even if the skipped reaction cuvette is cleaned and dried several times in an ordinary manner. In addition, there is a possibility that such a reaction cuvette comes again for a measurement of the analysis item to be affected by the remaining components. Therefore, when such unremoved component existence and a possible use of the same reaction cuvette in an affectable manner are understood to occur in advance, a dedicated detergent may be put into the skipped reaction cuvette and kept until the next cleaning and dry occasion. That is, the skipped reaction cuvette may be macerated in the dedicated detergent as an additional cleaning.

As described above, in some cases, remaining components on a reaction cuvette used for a measurement of an affecting analysis item may affect an analysis (or measurement) result of an analysis item to be affected by the remaining components if the reaction cuvette is also used for the measurement of the analysis item to be affected. The dedicated detergent may be required to clean the remaining components. Further, if the reaction cuvette is skipped, a throughput of use of a plurality of reaction cuvettes is deteriorated.

SUMMARY OF THE INVENTION

According to a first aspect of the present invention, there is provided a clinical laboratory apparatus. The apparatus includes a plurality of reaction cuvettes, a first dispenser, a second dispenser, a controller, and an analyzer. A subject sample and a reagent are mixed in each of the plurality of reaction cuvettes. The first dispenser is configured to dispense the subject sample into each of the plurality of reaction cuvettes. The second dispenser is configured to dispense the reagent into each of the plurality of reaction cuvettes so that the subject sample and the reagent are mixed. The controller is configured to categorize the plurality of reaction cuvettes into at least first and second groups, to designate at least first and second analysis items among two or more analysis items with respect to the subject sample, to control the second dispenser to avoid dispensing the reagent relevant to the first analysis item into the second group of the reaction cuvettes. The analyzer is configured to analyze a mixed result.

According to a second aspect of the present invention, there is provided a method of controlling a reagent dispensation in a clinical laboratory apparatus. The clinical laboratory apparatus includes a plurality of reaction cuvettes, a first dispenser, a second dispenser, and an analyzer. A subject sample and a reagent are mixed in each of the plurality of reaction cuvettes. The first dispenser is configured to dispense the subject sample into each of the plurality of reaction cuvettes. The second dispenser is configured to dispense the reagent into each of the plurality of reaction cuvettes so that the subject sample and the reagent are mixed. The analyzer is configured to analyze a mixed result. The method begins by categorizing the plurality of reaction cuvettes into at least first and second groups and designating at least first and second analysis items among two or more analysis items with respect to the subject sample. The method continues by controlling the second dispenser to avoid dispensing the reagent relevant to the first analysis item into the second group of the reaction cuvettes and dispensing the reagent relevant to the second analysis item into the first group of the reaction cuvettes.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

Figure 1:
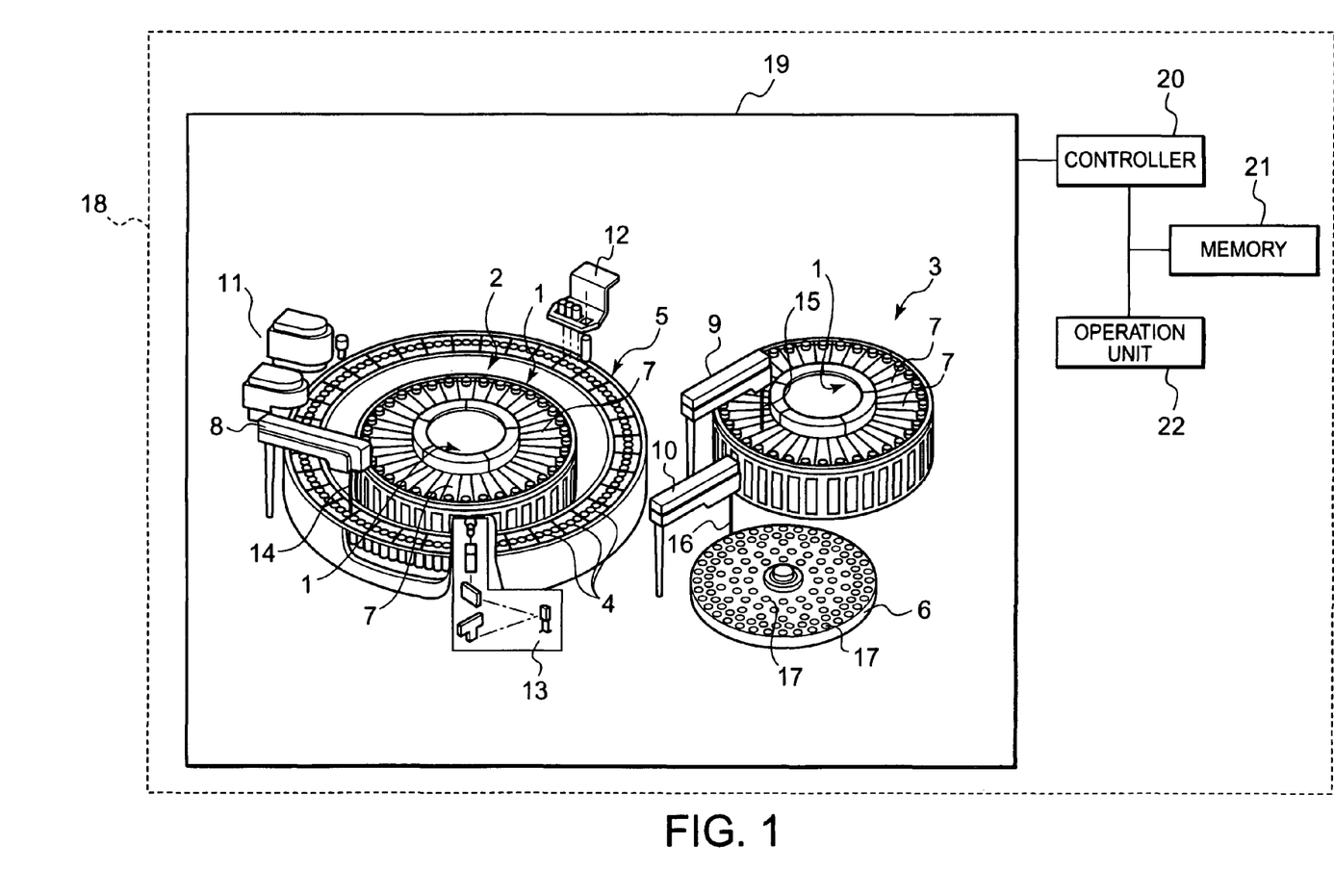
FIG. 1 illustrates an exemplary configuration of a clinical laboratory apparatus.

FIG. 1 illustrates an exemplary configuration of a clinical laboratory apparatus. As shown in FIG. 1, a clinical laboratory apparatus 18 may include an analysis unit 19, a controller 20, a memory 21, and an operation unit 22. The analysis unit 19 analyzes a subject sample. The controller 20 controls the analysis unit 19 and implements various information processing. The memory 21 stores information. The operation unit 22 is used for inputting information so as to operate the clinical laboratory apparatus 18.

The analysis unit 19 may includes reagent racks 1, reagent storages 2 and 3, reaction cuvettes 4, a reaction disk 5, a disk sampler 6, reagent bottles 7, the first reagent dispensing arm 8, the second reagent dispensing arm 9, a dispensing arm 10, a mixing unit 11, a cleaning unit 12, a photometer unit 13, the first reagent dispensing probe 14, the second reagent dispensing probe 15, a dispensing probe 16, and subject sample containers 17.

The reagent racks 1 house a plurality of reagent bottles 7. The reagent storages 2 and 3 are capable of housing the reagent racks 1, respectively. The reaction disk 5 formed like a ring places the reaction cuvettes 4 in a circumferential fashion. The disk sampler 6 places the subject sample containers 17. The reagent storages 2 and 3, the reaction disk 5, and the disk sampler 6 can be rotated by one or more driving units (not shown in FIG. 1). The reagent bottles 7 have reagent reacting to various components of the subject sample. The first and second reagent dispensing arms 8 and 9 dispense the reagent into the reaction cuvettes 4. The dispensing arm 10 dispenses the subject samples into the reaction cuvettes 4. The mixing unit 11 mixes or stirs the dispensed reagent and subject sample. The cleaning unit 12 cleans and dries the reaction cuvettes 4. The photometer unit 13 illuminates light to the reaction cuvettes 4 and measures absorbance transformation of the mixed reagent and subject sample. The first reagent dispensing probe 14 is provided at an end of the first reagent dispensing arm 8 so as to dispense the reagent to the reaction cuvettes 4. Similarly, the second reagent dispensing probe 15 is provided at an end of the second reagent dispensing arm 9 so as to dispense the reagent to the reaction cuvettes 4. The dispensing probe 16 is provided at an end of the dispensing arm 10 so as to dispense the subject sample to the reaction cuvettes 4. The subject sample container 17 has the subject samples.

A basic operation of the analysis unit 19 is as follows. The subject sample in the subject sample container 17 is dispensed to the reaction cuvettes 4 placed in the reaction disk 5 by the dispensing probe 16 provided at the dispensing arm 10. The reagent in the reagent bottles 7 which is relevant to measurements of one or more analysis items with respect to the subject sample is dispensed to the reaction cuvettes 4 placed in the reaction disk 5 by the first reagent dispensing probe 14 provided at the first reagent dispensing arm 8 and/or the second reagent dispensing probe 15 provided at the second reagent dispensing arm 9.

The reaction cuvettes 4 in which the subject sample and the reagent are dispensed are brought to the mixing unit 11 by the rotation of the reaction disk 5. The subject sample and the reagent in the reaction cuvettes 4 are stirred and mixed for making them to react to each other. The reaction cuvettes 4 are then brought to a photometry position of the photometer unit 13 by the rotation of the reaction disk 5. One or more particular components included in the reacted subject (i.e., the mixed subject sample and reagent) are measured for analysis by the photometer unit 13. After the measurement, the reaction cuvettes 4 are brought to the cleaning unit 12 so as to be cleaned and dried for further use. The content of the reaction cuvettes 4 may be disposed before the cleaning.

The controller 20 renders each unit of the analysis unit 19 to be operative in a predetermined sequence in accordance with instruction signals input from the operation unit 22. The controller 20 may also have various information processing features including a control of making item information of each analysis item to be measured to be stored in the memory 21.

The operation unit 22 includes, for example, one or more of a keyboard, a mouse, instruction buttons, switches, a joy stick, a track ball, and a touch key panel. By operating the above means, various types of information or instruction can be input to the clinical laboratory apparatus 18.

Figure 2:
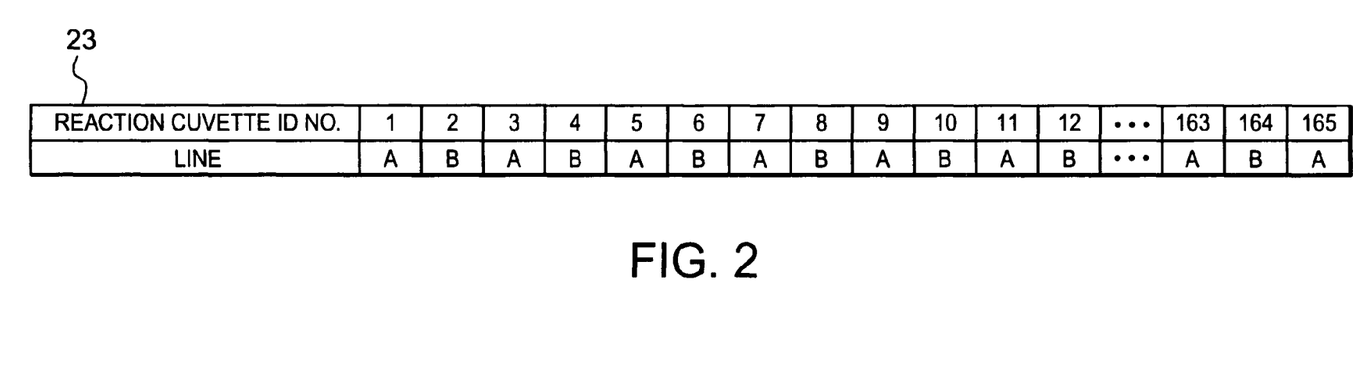
FIG. 2 illustrates a reaction cuvette line information table showing a relationship between reaction cuvette ID numbers and lines.

FIG. 2 illustrates a reaction cuvette line information table 23 showing a relationship between reaction cuvette identification (ID) numbers and lines. The lines are assigned to the reaction cuvette ID numbers as groups of the reaction cuvettes 4. Although each of the reaction cuvette ID numbers is categorized to one of two lines A and B in FIG. 2, the number of lines is not limited to two. The reaction cuvette line information table 23 may be input or instructed through the operation unit 22 and stored in the memory 21. For example, the necessary number of lines may be instructed from the operation unit 22, and in response, the lines are automatically assigned to the reaction cuvette ID numbers by the controller 20. Alternatively, an operator of the clinical laboratory apparatus 18 may input and assign a line A or B to the reaction cuvettes ID numbers. The reaction cuvette line information table 23 may be stored in the memory 21.

FIG. 2 is an example of a case that one hundred and sixty-five reaction cuvettes 4 are provided in a single line along the ring-formed reaction disk 5. Each of the reaction cuvettes 4 is given a unique reaction cuvette ID number from among one to one hundred and sixty-five. Once one of the reaction cuvette 4 has been given the reaction cuvette ID number '1', all the rest of the reaction cuvettes 4 may be inevitably given their reaction cuvette ID numbers. That is, the reaction cuvette 4 placed next to the reaction cuvette 4 given the reaction cuvette ID number '1' is given the reaction cuvette ID number '2'. In a similar manner, the reaction cuvette ID numbers '3' to '165' are given to the rest of the reaction cuvettes 4 in turn. Then, the reaction cuvettes 4 given odd numbers are categorized to a line A (or a group A). The reaction cuvettes 4 given even numbers are categorized to a line B (or a group B).

In practice, before measurements of one subject sample, it may not be known which of the reaction cuvette 4 to use first for dispensing the subject sample and the reagent. The reaction cuvette 4 to use first may be determined in accordance with the use of reaction cuvettes 4 in measurements of a previous subject sample. In other words, a plurality of analysis items are typically measured for one subject sample. One reaction cuvette 4 is assigned to one analysis item. Therefore, when three analysis items are measured, for example, for a subject sample A with the reaction cuvettes 4 given the reaction cuvette ID numbers '33' to '35', the reaction cuvette 4 given the reaction cuvette ID number '36' is the first one to use for the first analysis item of the next subject sample B, in principle. In this principle, the reaction cuvette 4 to use for the second analysis item of the subject sample B can be the reaction cuvette 4 given the reaction cuvette ID number '37'. Similar rules are applied, in principle, for the rest of the analysis items of the subject sample B.

After use of the reaction cuvette 4 given the reaction cuvette ID number '165', the reaction cuvette 4 given the reaction cuvette ID number '1' may be used since they are provided in a single line in the ring-formed reaction disk 5.

Figure 3:
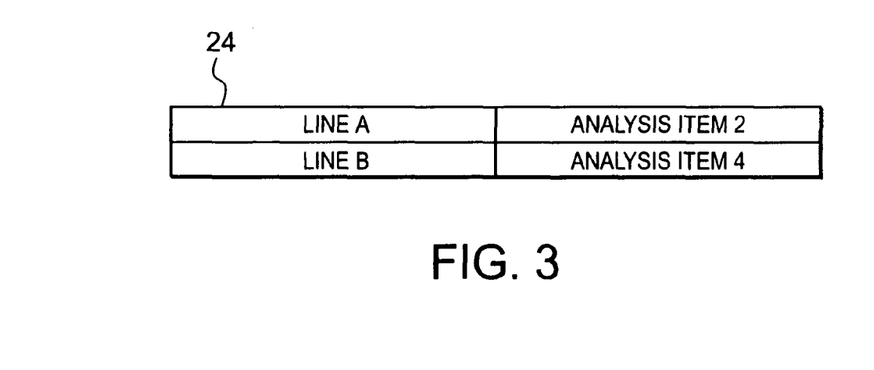
FIG. 3 illustrates a designated item line information table showing a relationship between lines and analysis items.

FIG. 3 illustrates a designated item line information table 24 showing a relationship between lines and analysis items. The analysis items shown in the designated item line information table 24 are those required to be measured in different reaction cuvettes 4.

The clinical laboratory apparatus 18 can typically measure and analyze the subject sample with reagent for various analysis items, for example, fifty items from an analysis item 1 to an analysis item 50. FIG. 3 shows that analysis items 2 and 4 are required to be measured in different reaction cuvettes 4. The analysis item 2 may affect the analysis item 4 through the reaction cuvette 4. Alternatively, the analysis item 4 may affect the analysis item 2 through the reaction cuvette 4. As another alternative example, the analysis items 2 and 4 may affect each other through the reaction cuvette 4. The relationship between the analysis items 2 and 4 is that one analysis item may be an affecting or affectable (hereinafter referred to as affecting) item and the other analysis item may be an affected item.

In detail, the first relationship between the analysis items 2 and 4 may be as follows. One or more components of reagent, used to measure the analysis item 2, remaining in the reaction cuvette 4 may act or behave something to affect a result of a measurement of the analysis item 4 if the measurement of the analysis item 4 is conducted with the same reaction cuvette 4. One example of the action (behavior) is that the one or more remaining components may react to one or more components of reagent used to measure the analysis item 4, to a subject sample with respect to the analysis item 4, and/or to one or more components of a mixed (or reacted) result of the reagent and the subject sample with respect to the analysis item 4. Another example of the action (behavior) is that the one or more components of reagent, used to measure the analysis item 2, remaining in the reaction cuvette 4 may disturb at least part of reaction between the reagent and the subject sample with respect to the analysis item 4. In both examples, the result of the measurement of the analysis item 4 may be affected by the one or more components of reagent, used to measure the analysis item 2, remaining in the reaction cuvette 4.

The second relationship between the analysis items 2 and 4 may be as follows. One or more components of reagent, used to measure the analysis item 4, remaining in the reaction cuvette 4 may act or behave something to affect a result of a measurement of the analysis item 2 if the measurement of the analysis item 2 is conducted with the same reaction cuvette 4. One example of the action (behavior) is that the one or more remaining components may react to one or more components of reagent used to measure the analysis item 2, to a subject sample with respect to the analysis item 2, and/or to one or more components of a mixed (or reacted) result of the reagent and the subject sample with respect to the analysis item 2. Another example of the action (behavior) is that the one or more components of reagent, used to measure the analysis item 4, remaining in the reaction cuvette 4 may disturb at least part of reaction between the reagent and the subject sample with respect to the analysis item 2. In both examples, the result of the measurement of the analysis item 2 may be affected by the one or more components of reagent, used to measure the analysis item 4, remaining in the reaction cuvette 4.

Although only one of the first and second relationships described above is enough to establish an affecting and affected relationship, the analysis items 2 and 4 may have a mutually affecting and affected relationship. That is, both of the first and second relationships may exist between the analysis items 2 and 4.

In the above description, the remaining components mean components which have not been removed from the reaction cuvette 4 in the ordinary cleaning and dry operation by the cleaning unit 12.

As shown in FIG. 3, since the analysis items 2 and 4 are required to be measured in different reaction cuvettes 4 because of the above reasons, the analysis item 2 is designated to the line A while the analysis item 4 is designated to the line B. Accordingly, the reaction cuvette 4 to be used to measure the analysis item 2 can always be controlled to be the reaction cuvette 4 categorized to the line A in the reaction cuvette line information table 23. Similarly, the reaction cuvette 4 to be used to measure the analysis item 4 can always be controlled to be the reaction cuvette 4 categorized to the line B in the reaction cuvette line information table 23. As a result, any one reaction cuvette 4 is never shared in the measurements of the analysis items 2 and 4 unless such reaction cuvette 4 is cleaned with the dedicated detergent.

In FIG. 3, the analysis item 2 may alternatively be designated to the line B while the analysis item 4 may alternatively be designated to the line A.

If there is another pair of an affecting analysis item and an affected analysis item which are neither affecting nor affected by the analysis items 2 and 4, such affecting analysis item and affected analysis item can also be designated to the lines A and B, respectively.

Further, if there is another analysis item which is affecting at least one of the analysis items 2 and 4 and/or is affected by at least one of the analysis items 2 and 4, another line C is required and such another analysis item is designated to the line C. In this case, lines A, B, and C may repeatedly be assigned to the reaction cuvette ID numbers one to one hundred and sixty-five, in the reaction cuvette line information table 23. If it is necessary to change the line assignment from A and B to A, B, and C, it may be necessary to clean all the reaction cuvettes 4 with the dedicated detergent so as to remove the remaining components. Otherwise, it may happen that one reaction cuvette 4 newly categorized to the line A used to be categorized to the line B and affects a measurement of the analysis item 2 when the one reaction cuvette 4 is used to measure the analysis item 2. To avoid this problem without cleaning with the dedicated detergent, it may be necessary to determine possible number of lines and categorize the reaction cuvette ID numbers into the determined number of lines in the reaction cuvette line information table 23 in advance, considering all the types of analysis items and their affecting/affected relationships.

Figure 4:
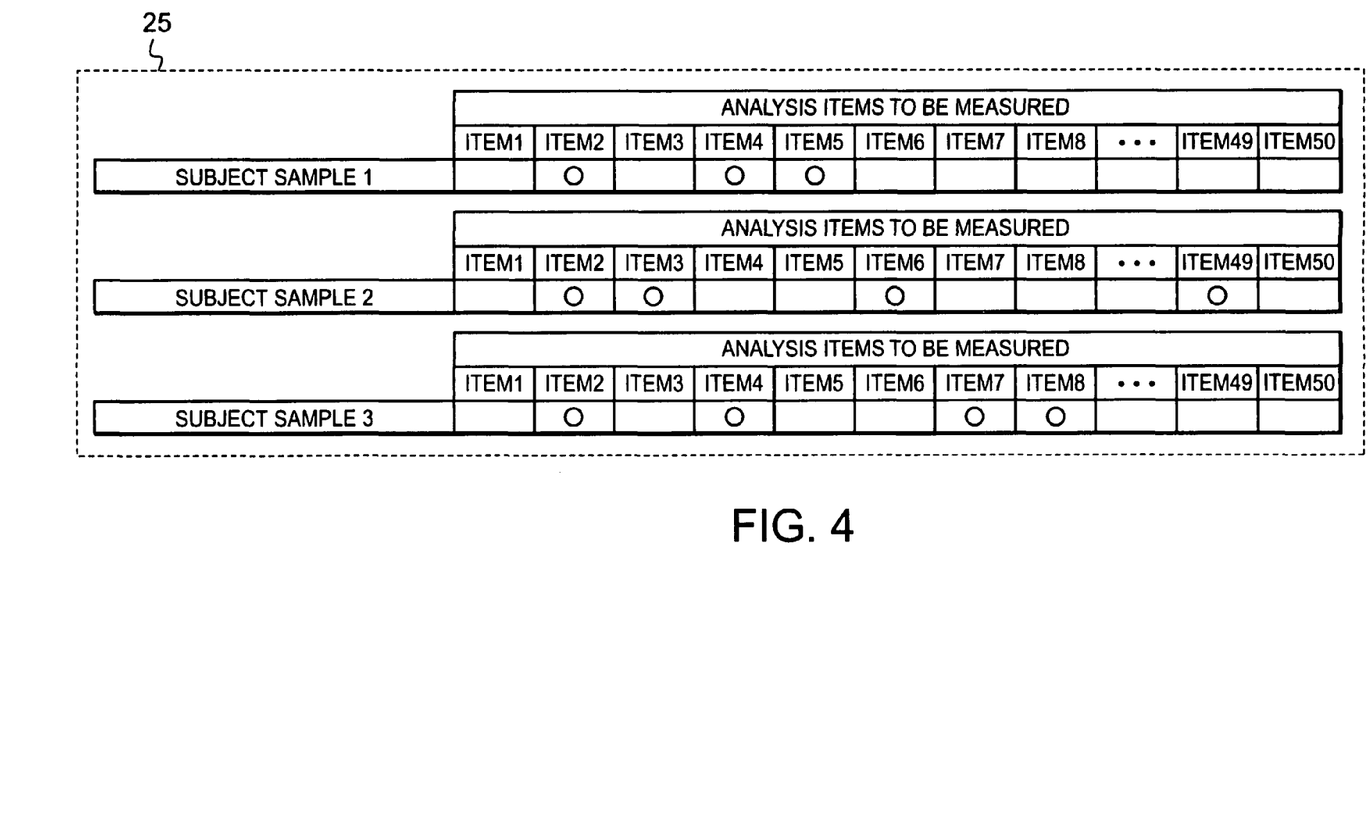
FIG. 4 illustrates an analysis request information table showing requested analysis items with respect to each subject sample.

FIG. 4 illustrates an analysis request information table 25 showing requested analysis items with respect to each subject sample. In FIG. 4, it is requested to measure the analysis items 2, 4, and 5 with respect to a subject sample 1. It is also requested to measure the analysis items 2, 3, 6, and 49 with respect to a subject sample 2. In addition, it is requested to measure the analysis items 2, 4, 7, and 8 with respect to a subject sample 3.

When the analysis item 1 has a top priority in the measurement order while the analysis item 50 has a least priority, the measurements are basically conducted in the order of the analysis items 2, 4, and 5 with respect to the subject sample 1, the analysis items 2, 3, 6, and 49 with respect to the subject sample 2, and the analysis items 2, 4, 7, and 8 with respect to the subject sample 3, according to a principle. This order, however, may be altered so as to avoid the affecting problem described above.

Figure 5:
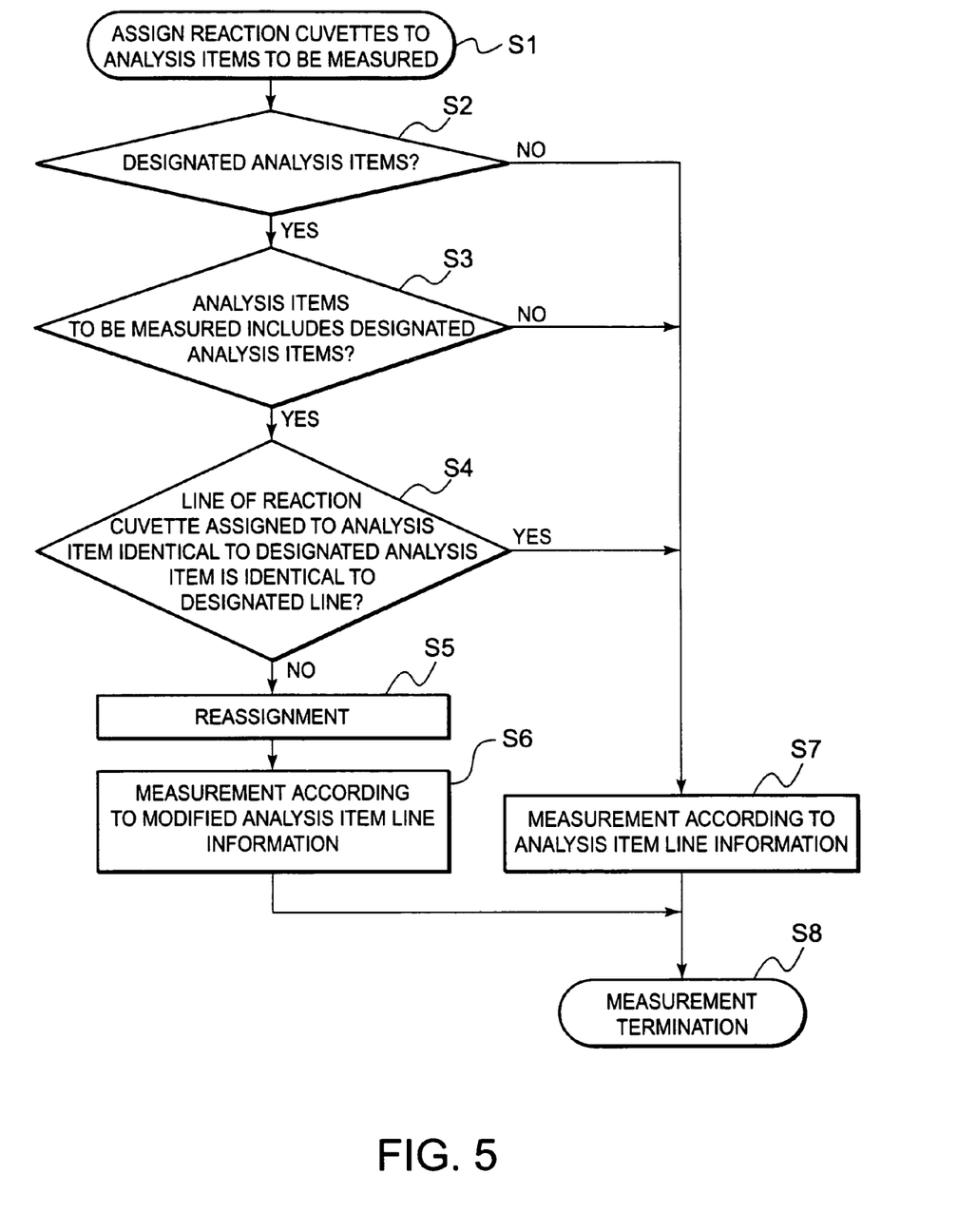
FIG. 5 is a flowchart for explaining an exemplary procedure of measurements of analysis items.

FIG. 5 is a flowchart for explaining an exemplary procedure of measurements of analysis items. The procedure may be implemented by the controller 20 in accordance with a control program stored in the memory 21 and the information, for example, as shown in FIGS. 2 and 3, stored in the memory 21.

The operator of the clinical laboratory system 18 operates the operation unit 22 to input a start command so that measurements of desired analysis items begin with respect to subject samples obtained from one or more specimens such as, for example, patients. The operator further inputs information to select the desired analysis items by, for example, directly inputting information of desired analysis items or their item numbers, pressing buttons corresponding to the desired analysis items on the operation unit 22, or clicking on icons corresponding to the desired analysis items in a monitor of the clinical laboratory apparatus 18. Based on the selection, the analysis request information table 25 is prepared as shown in FIG. 4.

Figure 6:
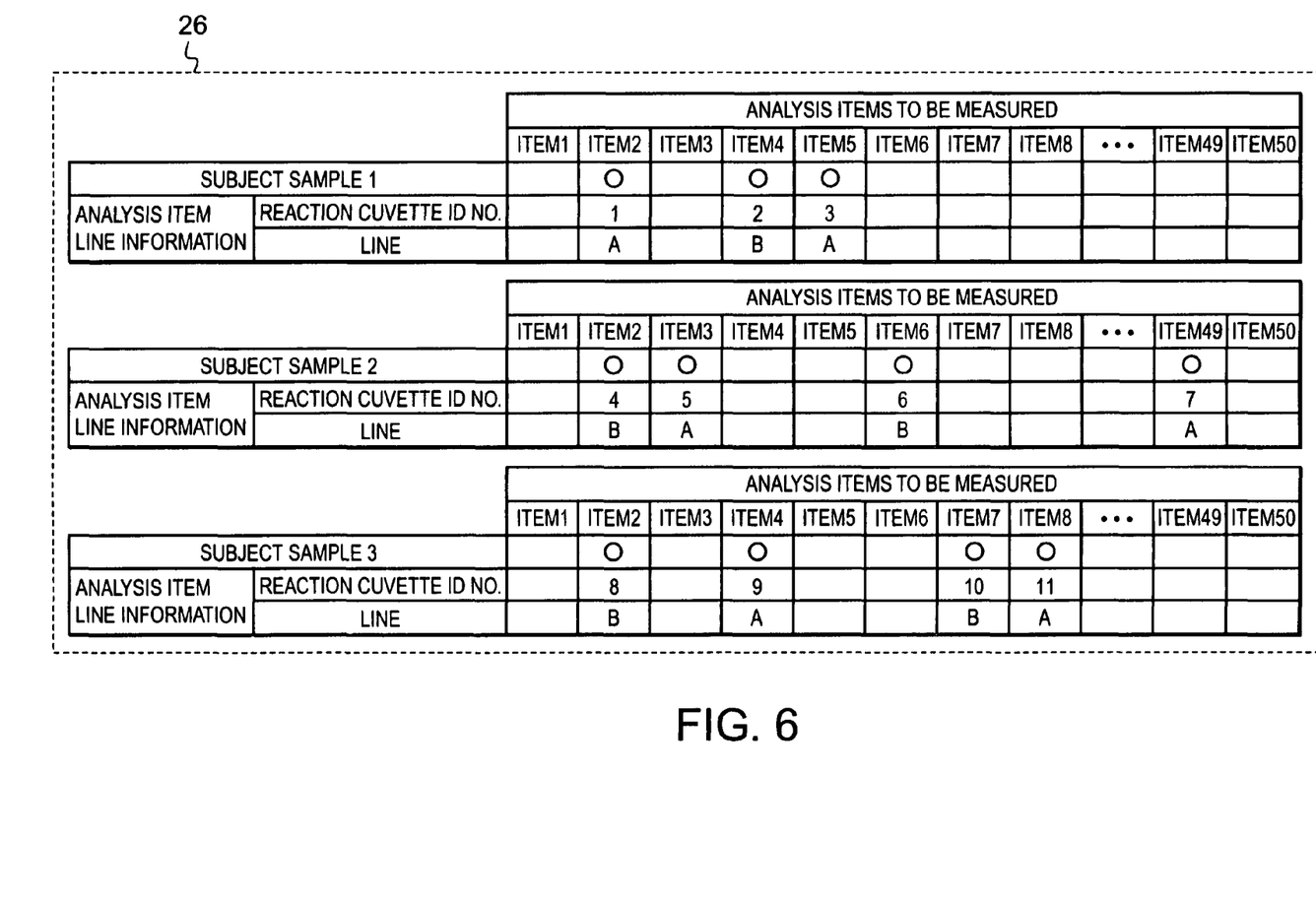
FIG. 6 illustrates an analysis item line information table showing an exemplary assignment of reaction cuvette ID numbers to analysis items to be measured.

Based on the reaction cuvette line information table 23 and the analysis request information table 25, the controller 20 prepares an analysis item line information table 26 as shown in FIG. 6 by assigning the reaction cuvette line information as analysis item line information to the selected analysis items (or analysis items to be measured) (step S1). In FIG. 6, the analysis item line information may include the reaction cuvette ID numbers and line information as similar to the reaction cuvette line information. The analysis item 2 is assigned to the reaction cuvette ID number '1' in FIG. 6, but this is only an example. As already described, the reaction cuvette ID number to be assigned to the first analysis item (the analysis item 2 in FIG. 6) may be determined in accordance with the use of the reaction cuvettes 4 in measurements of a previous subject sample (see also FIG. 9).

Once the reaction cuvette ID number is determined for the analysis item 2, other analysis items to be measured may inevitably be assigned to the following reaction cuvette ID numbers at this stage as shown in FIG. 6.

The controller 20 then refers to the designated item line information table 24 so as to determine if there are designated analysis items or not (step S2). If there is no designated analysis item in the designated item line information table 24, the procedure proceeds to step S7. Step S7 will be described later.

According to the designated item line information table 24 shown in FIG. 3, the controller 20 determines that there are two designated analysis items, i.e., the analysis item 2 designated to the line A and the analysis item 4 designated to the line B. Responsive to the determination, the controller 20 further refers to the analysis item line information table 26 and determines whether the designated analysis items 2 and 4 are included (or selected) as the analysis items to be measured in the analysis item line information table 26 (step S3). If no designated analysis item is included in the analysis item line information table 26, the procedure proceeds to step S7.

According to the analysis item line information table 26 shown in FIG. 6, the controller 20 determines that the designated analysis items 2 and 4 are included as the analysis items to be measured in the analysis item line information table 26.

The controller 20 compares the lines of the reaction cuvette ID numbers assigned to the analysis items 2 and 4 in the analysis item line information table 26 to the lines designated to the analysis items 2 and 4 in the designated item line information table 24. The controller 20 determines whether the lines of the reaction cuvette ID numbers assigned to the analysis items 2 and 4 in the analysis item line information table 26 are identical to the lines designated to the analysis items 2 and 4 in the designated item line information table 24 (step 4). If all the lines in the analysis item line information table 26 are identical to the designated lines, the procedure proceeds to step S7.

According to the analysis item line information table 26 shown in FIG. 6, the controller 20 determines that the lines of the reaction cuvette ID numbers assigned to the analysis items 2 and 4 are not identical to the designated lines in part. For example, the analysis items 2 and 4 selected with respect to the subject sample 1 are assigned to the lines A and B, respectively, which are identical to the designated line information in the designated item line information table 24. However, the analysis item 2 selected with respect to the subject sample 2 is assigned to the line B, which is not identical to the line information (i.e. line A) in the designated item line information table 24, as shown in FIG. 6. Also, the analysis items 2 and 4 selected with respect to the subject sample 3 are assigned to the lines B and A, respectively, which are not identical to the designated line information (i.e. line A and line B) in the designated item line information table 24.

The controller 20 alters the line assignment for the above analysis item 2 with respect to the subject sample 2 and the analysis items 2 and 4 with respect to the subject sample 3 by reassigning the reaction cuvette ID numbers to these analysis items (step S5).

Figure 7:
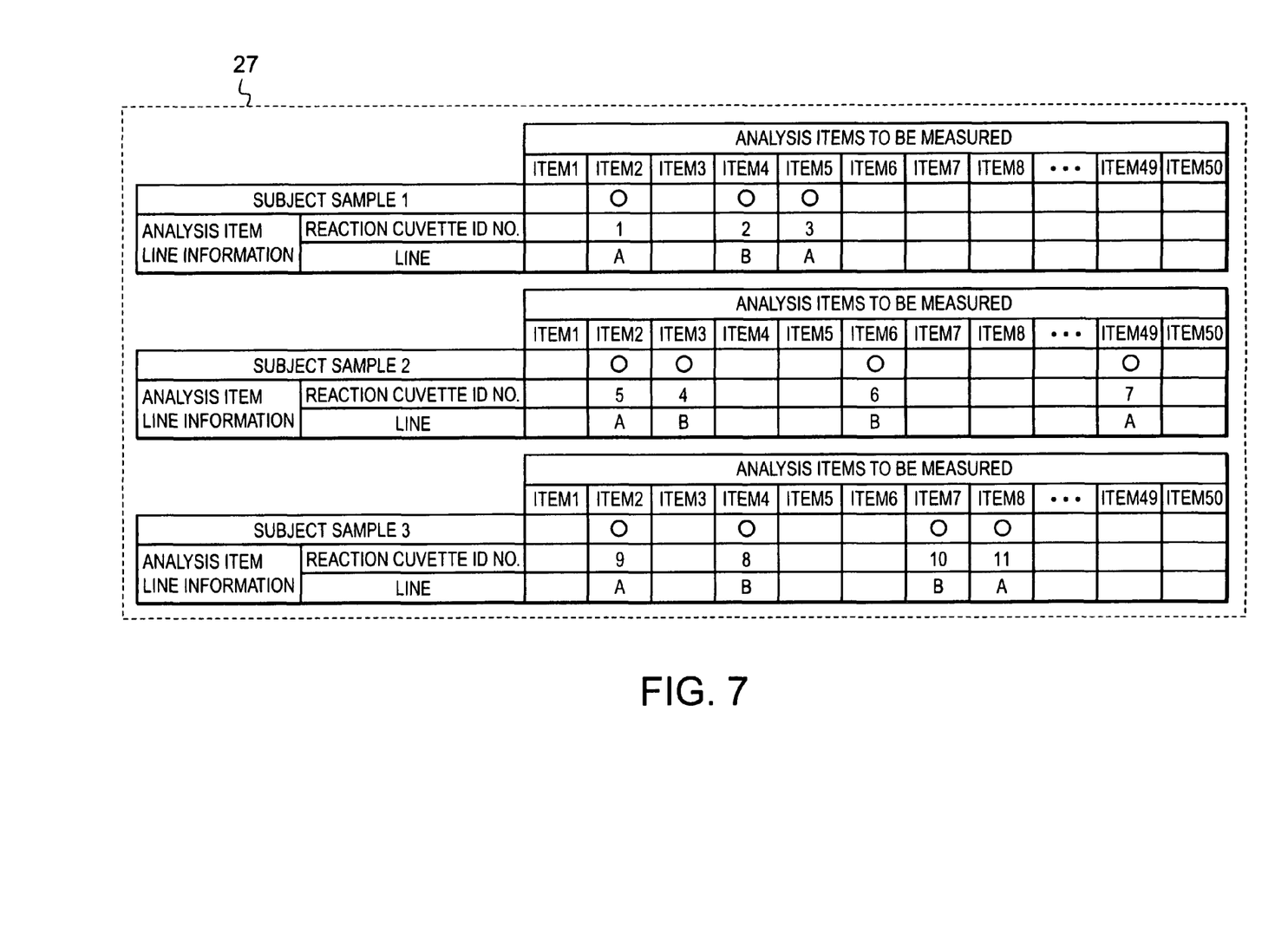
FIG. 7 illustrates a modified analysis item line information table showing reassigned reaction cuvette ID numbers.

For example, the controller 20 may counterchange the reaction cuvette ID number originally assigned to the analysis item which is required to change the line and the reaction cuvette ID number originally assigned to the analysis item which is not designated in the designated item line information table 24. As shown in FIG. 7, the reaction cuvette '4' categorized to the line B which was assigned to the analysis item 2 with respect to the subject sample 2 is reassigned to the analysis item 3 with respect to the subject sample 2. In exchange for this reassignment, the reaction cuvette '5' categorized to the line A which was assigned to the analysis item 3 with respect to the subject sample 2 is reassigned to the analysis item 2 with respect to the subject sample 2. Accordingly, the line A reassigned to the analysis item 2 with respect to the subject sample 2 becomes identical to the designated line in the designated item line information table 24.

As another example, the controller 20 may counterchange the reaction cuvette ID number originally assigned to the analysis item which is required to change the line and the reaction cuvette ID number originally assigned to the analysis item which is also required to change the line. As shown in FIG. 7, the reaction cuvette '8' categorized to the line B which was assigned to the analysis item 2 with respect to the subject sample 3 is reassigned to the analysis item 4 with respect to the subject sample 3. In exchange for this reassignment, the reaction cuvette '9' categorized to the line A which was assigned to the analysis item 4 with respect to the subject sample 3 is reassigned to the analysis item 2 with respect to the subject sample 3. Accordingly, the line A reassigned to the analysis item 2 with respect to the subject sample 3 becomes identical to the designated line in the designated item line information table 24. Also the line B reassigned to the analysis item 2 with respect to the subject sample 3 becomes identical to the designated line in the designated item line information table 24. In this example, the exchange may preferably be implemented between two analysis items with respect to the same subject sample.

Reassignment by the controller 20 is not limited to the above two examples, but may be accomplished by any other possible ways. Such possible ways include an example shown in FIG. 8 and an exchange with the reaction cuvette ID number which is not assigned to any analysis item as long as the line assigned to the reaction cuvette ID number is appropriate for the exchange.

After the reassignment by the controller 20, measurements of the analysis items may be conducted with reaction cuvettes 4 in a predetermined order in accordance with a modified analysis item line information table 27 shown in FIG. 7 (step S6). Since the reaction cuvettes 4 are provided in the reaction disk 5 in the order of the reaction cuvette ID numbers, the measurements are basically conducted from the analysis item 2 with respect to the subject sample 1. After the measurement of the analysis item 5 with respect to the subject sample 1, the measurement may be conducted on the analysis item 3 with respect to the subject sample 2. The analysis item 2 with respect to the subject sample 2 may be measured after the analysis item 3 with respect to the subject sample 2. The measurement of the analysis item 2 with respect to the subject sample 2 is conducted with the reaction cuvette 4 given the reaction cuvette ID number 5 categorized to the line A.

Similarly, after the measurement of the analysis item 4 with respect to the subject sample 2, the measurement may be conducted on the analysis item 4 with respect to the subject sample 3. The analysis item 2 with respect to the subject sample 3 may be measured after the analysis item 4 with respect to the subject sample 3. The measurement of the analysis item 4 with respect to the subject sample 3 is conducted with the reaction cuvette 4 given the reaction cuvette ID number 8 categorized to the line B. The measurement of the analysis item 2 with respect to the subject sample 3 is conducted with the reaction cuvette 4 given the reaction cuvette ID number 9 categorized to the line A.

In step S7, measurements of the analysis items may be conducted with reaction cuvettes 4 in a predetermined order in accordance with the analysis item line information table 26 shown in FIG. 6. The measurements are basically conducted from the analysis item 2 with respect to the subject sample 1 and continues in the order of the reaction cuvette ID numbers assigned to the analysis items to be measured.

After all the measurements according to the analysis item line information table 26 or the modified analysis item line information table 27, the procedure of the measurements of analysis items is terminated in the analysis unit 19 (step S8).

In the above description, the reassignment of the reaction cuvette ID numbers has been accomplished by exchanging two reaction cuvette ID numbers. Another reassignment example of the reaction cuvette ID numbers will be described with reference to FIG. 8.

Figure 8:
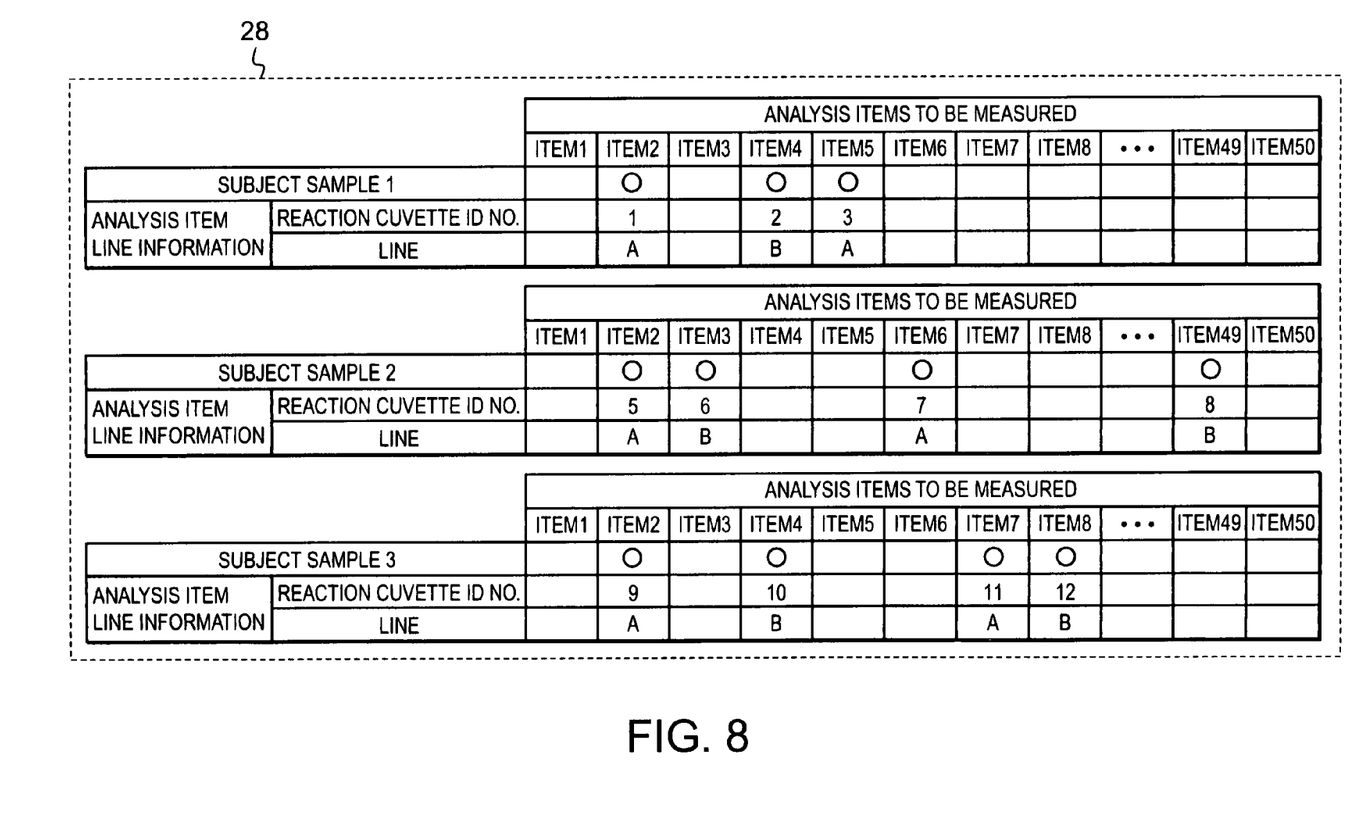
FIG. 8 illustrates another modified analysis item line information table showing reassigned reaction cuvette ID numbers.

FIG. 8 illustrates another modified analysis item line information table 28 showing reassigned reaction cuvette ID numbers. In FIG. 8, the analysis items to be measured are the same as those shown in FIG. 7. The reassignment is also conducted based on the designated item line information table 24 shown in FIG. 3.

As understood from the modified analysis item line information table 28 shown in FIG. 8, the reaction cuvette ID number '4' categorized to the line B is skipped so as not to be assigned to the analysis item 2 with respect to the subject sample 2. Accordingly, the rest of the analysis items are assigned to one-number shifted reaction cuvette ID numbers. As a result, the analysis item 2 with respect to the subject sample 2 is assigned to the reaction cuvette ID number '5' categorized to the line A. Similarly, the analysis items 2 and 4 with respect to the subject sample 3 are inevitably assigned to the reaction cuvette ID numbers '9' and '10' categorized to the lines A and B, respectively.

Even after the skip of one reaction cuvette ID number, another reaction cuvette ID number may also be skipped according to the necessity.

As described above, the reaction cuvette 4 which was used to measure an affecting analysis item is never used to measure an affected analysis item through the reaction cuvettes 4 according to the embodiments described above. Therefore, it may be possible to improve accuracy of the analysis result. In addition, the dedicated detergent is not needed or may be less often required, compared to the prior art. This also leads to improvement of a throughput of the measurements since there are few chances to skip the reaction cuvettes for the purpose of cleaning with the dedicated detergent. Particularly, when the reassignment is accomplished in accordance with the embodiment shown in FIG. 7, the throughput can be improved. In other words, the measurement efficiency can be improved according to the embodiment.

In the above embodiments, it has been described that the reaction cuvettes 4 are provided in a single line along the reaction disk 5. For example, however, the reassignment technique described above may be applied when the reaction cuvettes 4 are provided in double lines along the reaction disk 5. In this example, the reassignment may be implemented for each reaction cuvette line.

Figure 9:
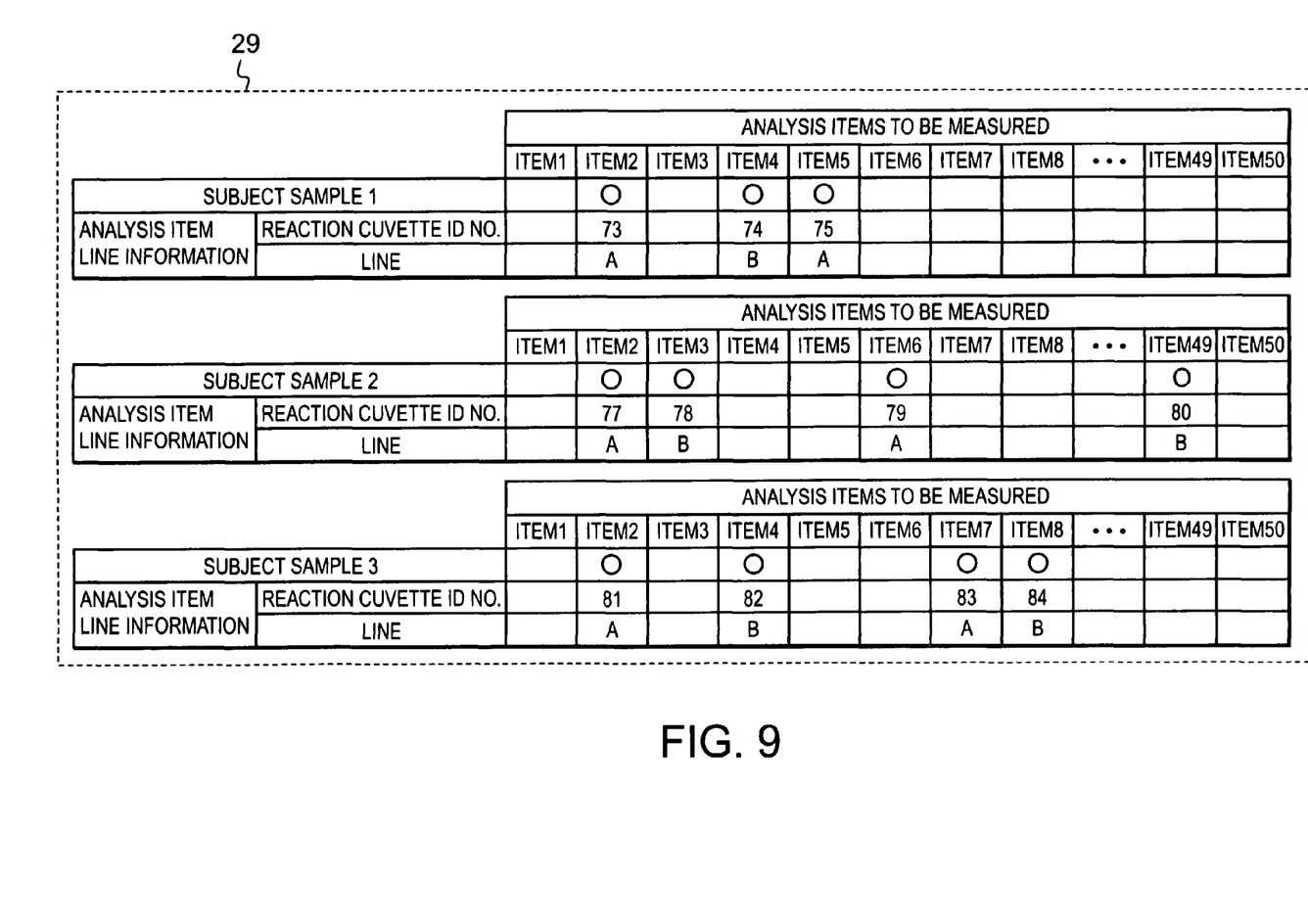
FIG. 9 illustrates another modified analysis item line information table corresponding to the modified analysis item line information table shown in FIG. 8.

Further, as shown in FIG. 9 which illustrates another modified analysis item line information table 29 corresponding to the modified analysis item line information table 28 shown in FIG. 8, the analysis item 2 to be measured first may be assigned to any reaction cuvette ID number (e.g., '73') other than one '1'.

Instead of reassigning after determining the measurement order by setting a priority order in advance of the measurement, the measurement may be initiated without setting the priority order. In this case, at the time when a reaction cuvette ID number of the reaction cuvette to be used for the first analysis item to be measured has been determined for a subject sample, an analysis item which cannot be affected through the reaction cuvette 4 may be measured with a reaction cuvette 4 given the reaction cuvette ID number by allowing to access any reagent. This may be conducted for each subject sample. This measurement may require another configuration to the clinical laboratory apparatus 18. Another configuration may require to be accessible to specific reagent appropriate for the non-affected analysis item and to be capable of dispensing the reagent to the reaction cuvette 4. A control system for this measurement may, however, be more easily formed than developing a software for controlling there assignment, for example, shown in FIG. 7 since it requires only to store reaction cuvette line information and position information of each reagent in a corresponding manner and to control a reagent dispensing probe movement, a reagent suction, a reagent dispensation, and the like With reference to the stored information.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A clinical laboratory apparatus, comprising:
a plurality of reaction cuvettes;
a first dispenser configured to dispense a subject sample into each of the plurality of reaction cuvettes;
a second dispenser configured to dispense a reagent into each of the plurality of reaction cuvettes so that the subject sample and the reagent are mixed;
a controller configured to
categorize the plurality of reaction cuvettes into at least a first and a second group,
designate at least a first and a second analysis item among two or more analysis items associated with the subject sample to the first and second groups, respectively,
assign each of the plurality of reaction cuvettes to one of the two or more analysis items from which the first and second analysis items have been designated,
compare the categorized group of each of the plurality of reaction cuvettes assigned to the first and second analysis item to the designated groups of the first and second analysis items to determine whether the categorized group of the reaction cuvette is identical to the designated group of the analysis item assigned to the cuvette, and
if not identical cause the second dispenser to skip a first reaction cuvette and reassign a second reaction cuvette provided next to the first reaction cuvette to the first analysis item upon the determination that the first reaction cuvette, which was categorized in the second group, has been assigned to the first analysis item; and
an analyzer configured to analyze a mixed result.

2. The apparatus according to claim 1, wherein, when the plurality of reaction cuvettes are linearly provided, the reaction cuvettes provided in odd-number orders are categorized into the first group and the reaction cuvettes provided in even-number orders are categorized into the second group.

3. The apparatus according to claim 1, wherein the controller is configured to designate the first analysis item as an analysis item whose analysis result is affected through one of the plurality of reaction cuvettes used for the second analysis item if the one reaction cuvette is used for the first analysis item.

4. The clinical laboratory apparatus according to claim 1, wherein the controller is further configured to reassign the first reaction cuvette to the second analysis item and the second reaction cuvette to the first analysis item upon a determination that the first reaction cuvette, which has been assigned to the first analysis item, was categorized into the second group, and the second reaction cuvette, which has been assigned to the second analysis item, was categorized into the first group.

5. The clinical laboratory apparatus according to claim 1, wherein the controller is further configured to reassign the first reaction cuvette to a third analysis item other than the first and second analysis items and reassign the second reaction cuvette to the first analysis item, upon a determination that the first reaction cuvette, which has been assigned to the first analysis item, was categorized into the second group and that the second reaction cuvette has been assigned to the third analysis item and was categorized into the first group.

6. The apparatus according to claim 1, wherein, when the plurality of reaction cuvettes are linearly provided, the reaction cuvettes provided in odd-number orders are categorized into the first group and the reaction cuvettes provided in even-number orders are categorized into the second group, and the first reaction cuvette is provided in the even-number order.

7. The apparatus according to claim 1, further comprising an input unit configured to input an instruction, wherein the controller is configured to designate the at least first and second analysis items in accordance with the instruction.

8. The clinical laboratory apparatus according to claim 1, wherein the second reaction cuvette was categorized into the first group.

9. The clinical laboratory apparatus according to claim 1, wherein the two or more analysis items associated with the subject sample are assigned to adjacent ones of the plurality of reaction cuvettes.

* * * * *